United States Patent
Nakagawa et al.

(10) Patent No.: US 10,352,893 B2
(45) Date of Patent: Jul. 16, 2019

(54) GAS SENSOR CONTROL APPARATUS

(71) Applicant: NGK SPARK PLUG CO., LTD., Nagoya-shi, Aichi (JP)

(72) Inventors: Keisuke Nakagawa, Kiyosu (JP); Shigehiro Ohtsuka, Gifu (JP); Hisashi Kozuka, Ichinomiya (JP); Kazuma Ito, Komaki (JP); Ippei Kato, Komaki (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 75 days.

(21) Appl. No.: 15/250,143

(22) Filed: Aug. 29, 2016

(65) Prior Publication Data
US 2017/0059511 A1 Mar. 2, 2017

(30) Foreign Application Priority Data
Aug. 31, 2015 (JP) ................................ 2015-170214

(51) Int. Cl.
*G01N 27/406* (2006.01)
*G01N 27/407* (2006.01)

(52) U.S. Cl.
CPC ..... *G01N 27/4067* (2013.01); *G01N 27/4071* (2013.01); *G01N 27/4075* (2013.01)

(58) Field of Classification Search
CPC ......................................... G01N 27/406–4118
See application file for complete search history.

(56) References Cited

U.S. PATENT DOCUMENTS 6,060,420 A * 5/2000 Munakata ............ B01D 53/945
502/302
6,129,862 A 10/2000 Munakata et al.
(Continued)

FOREIGN PATENT DOCUMENTS

JP 8-130018 A 5/1996
JP 2002-181764 A 6/2002
(Continued)

OTHER PUBLICATIONS

Communication dated Oct. 23, 2018, from Japanese Patent Office in counterpart application No. 2015-170214.

*Primary Examiner* — Bach T Dinh
(74) *Attorney, Agent, or Firm* — Sughrue Mion, PLLC

(57) ABSTRACT

A gas sensor control apparatus including a gas sensor element, a heater for heating the gas sensor element, and heater energization control means for feedback controlling the supply of electric current to the heater such that the internal resistance of the gas sensor element coincides with a target resistance. The gas sensor element has a solid electrolyte member and an electrode portion including an outside electrode and an inside electrode. At least a portion of the electrode portion is formed of an electrically conductive oxide whose main component is (i) a first perovskite phase which is represented by a composition formula of $LaCo_{1-x}Ni_xO_{3\pm d}$ ($0.300 \le x \le 0.600$, $0 \le d \le 0.4$) and has a perovskite-type crystal structure, or (ii) a second perovskite phase which is represented by a composition formula of $LaFe_{1-y}Ni_yO_{3\pm d}$ ($0.450 \le y \le 0.700$, $0 \le d \le 0.4$) and has a perovskite-type crystal structure.

2 Claims, 7 Drawing Sheets

(56) References Cited

U.S. PATENT DOCUMENTS

| | | | |
|---|---|---|---|
| 6,623,618 B1* | 9/2003 | Kato | G01N 27/419 |
| | | | 204/425 |
| 9,136,033 B2 | 9/2015 | Kozuka et al. | |
| 2002/0017462 A1* | 2/2002 | Diehl | G01N 27/4075 |
| | | | 204/426 |
| 2002/0070736 A1 | 6/2002 | Nakae et al. | |
| 2003/0121801 A1* | 7/2003 | Inaba | G01N 27/4075 |
| | | | 205/785.5 |
| 2004/0047396 A1* | 3/2004 | Nomura | F02D 41/1476 |
| | | | 374/141 |
| 2004/0069655 A1* | 4/2004 | Chaput | B01D 53/228 |
| | | | 205/765 |
| 2015/0099142 A1 | 4/2015 | Kozuka et al. | |

FOREIGN PATENT DOCUMENTS

| | | | |
|---|---|---|---|
| JP | 2003-194773 A | 7/2003 |
| JP | 2009-63330 A | 3/2009 |
| JP | 2013-231659 A | 11/2013 |
| JP | WO2013/150779 A1 | 12/2015 |

* cited by examiner

GAS SENSOR CONTROL APPARATUS

BACKGROUND OF THE INVENTION

1. Field of the Invention

The present invention relates to a gas sensor control apparatus which includes a gas sensor element employing electrodes formed of an electrically conductive oxide.

2. Description of the Related Art

Conventionally, a gas sensor has been known which includes a gas sensor element whose electrical characteristic changes with the concentration of a particular gas component contained in a gas under measurement. For example, Patent Document 1 discloses a gas sensor element which includes a solid electrolyte member having the shape of a bottomed tube closed at its forward end; an inside electrode (a reference electrode) formed on the inner surface of the solid electrolyte member; and an outside electrode (a detection electrode) formed on a forward end portion of the outer surface of the solid electrolyte member. Such a gas sensor is suitably used for detecting the concentration of a particular gas contained in exhaust gas discharged from, for example, a combustor or an internal combustion engine.

Importantly, the output of a gas sensor greatly depends on the temperature of its gas sensor element (hereinafter referred to as the "element temperature"). Therefore, a technique of maintaining the element temperature within a predetermined temperature range (allowable range) has been used and within which the gas sensor element is in an active state (Patent Document 2). For example, a technique which utilizes a phenomenon whereby the element impedance (internal resistance) of the gas sensor element changes with the element temperature has been used. According to this technique, a heater for heating the gas sensor element is provided, and the supply of electric current to the heater is feedback-controlled such that the element impedance (internal resistance) becomes equal to a target impedance (target resistance) (hereinafter also referred to as an "internal resistance control"). Notably, in conventional gas sensor elements, from the viewpoint of, for example, durability and catalytic performance, a noble metal such as platinum (Pt) is often used as an electrode material.

[Patent Document 1] Japanese Patent Application Laid-Open (kokai) No. 2009-63330

[Patent Document 2] Japanese Patent Application Laid-Open (kokai) No. 2013-231659

3. Problem to be Solved by the Invention

However, it has been known that when internal resistance control is performed using a gas sensor element in which a noble metal such as platinum (Pt) serves as an electrode material, a change in the resistance of the electrode leads (hereinafter referred to as "lead resistance") with temperature may adversely affect the stability of the element temperature. In general, the internal resistance of a gas sensor element is represented by the sum of the lead resistance and a detection portion resistance (grain internal resistance+ grain boundary resistance+electrode interface resistance). For example, the resistance of platinum has a positive correlation with temperature, and the detection portion resistance has a negative correlation with temperature. In the case where the entire internal resistance has a negative correlation with temperature, the element temperature can be maintained within the predetermined range by controlling the internal resistance to a fixed value. However, since the resistance of platinum has a positive correlation with temperature, when the amount of change in the lead resistance with temperature is large, a problem arises in that even when internal resistance control is performed, the control accuracy of the element temperature is not sufficient. Consequently, the element temperature cannot be controlled to a predetermined range. Particularly, in the case where the amount of a noble metal such as platinum used as an electrode material is reduced for cost reduction whereby the lead resistance increases, the above-mentioned problem becomes remarkable.

SUMMARY OF THE INVENTION

The present invention has been made so as to solve the above-described problem, and an object thereof is to provide a gas sensor control apparatus which has excellent temperature control performance.

The above object has been achieved by providing (1) a gas sensor control apparatus comprising a gas sensor element which includes a solid electrolyte member and an electrode portion, the electrode portion including an outside electrode which is provided on an outer surface of the solid electrolyte member and which comes into contact with a gas under measurement, and an inside electrode which is provided on an inner surface of the solid electrolyte member and which comes into contact with a reference gas; a heater for heating the gas sensor element; and heater energization control means for feedback controlling energization of the heater such that an internal resistance of the gas sensor element coincides with a target resistance. At least a portion of the electrode portion is formed of an electrically conductive oxide whose main component is (i) a perovskite phase which is represented by a composition formula of $LaCo_{1-x}Ni_xO_{3\pm d}$ ($0.300 \leq x \leq 0.600$, $0 \leq d \leq 0.4$) and has a perovskite-type crystal structure, or (ii) a perovskite phase which is represented by a composition formula of $LaFe_{1-y}Ni_yO_{3\pm d}$ ($0.450 \leq y \leq 0.700$, $0 \leq d \leq 0.4$) and has a perovskite-type crystal structure.

Each of these perovskite phases; i.e., (i) the perovskite phase which is represented by a composition formula of $LaCo_{1-x}Ni_xO_{3\pm d}$ ($0.300 \leq x \leq 0.600$, $0 \leq d \leq 0.4$) and has a perovskite-type crystal structure (hereinafter referred to as LCN) and (ii) the perovskite phase which is represented by a composition formula of $LaFe_{1-y}Ni_yO_{3\pm d}$ ($0.450 \leq y \leq 0.700$, $0 \leq d \leq 0.4$) and has a perovskite-type crystal structure (hereinafter referred to as LFN), has a room temperature electrical conductivity of 200 S/cm or greater. In addition, the absolute value of the B constant (25° C. to 570° C.) of each of the perovskite phases is smaller than the absolute value of the B constant of platinum. In the above-described gas sensor element, at least a portion of the electrode portion is formed of an electrically conductive oxide whose main component is LCN or LFN. Therefore, the electrode portion can have a sufficiently high electrical conductivity, and when internal resistance control is performed, the element temperature can be controlled with increased accuracy.

In a preferred embodiment (2) of the gas sensor control apparatus (1) above, the gas sensor element is configured such that the outside electrode includes an outside lead portion and an outside detection electrode portion which comes into contact with the gas under measurement; the inside electrode includes an inside lead portion and an inside detection electrode portion which comes into contact with the reference gas; and at least one of the outside lead portion and the inside lead portion is formed of the electrically conductive oxide.

According to this configuration, at least one of the outside lead portion and the inside lead portion is formed of the electrically conductive oxide. Therefore, when internal resistance control is performed, the element temperature can be controlled in an improved manner.

The present invention can be realized in various forms. For example, the present invention can be realized as a gas sensor element, a gas sensor including the gas sensor element, a method of manufacturing the gas sensor element, or a method of manufacturing the gas sensor.

DESCRIPTION OF REFERENCE NUMERALS

Figure 1:
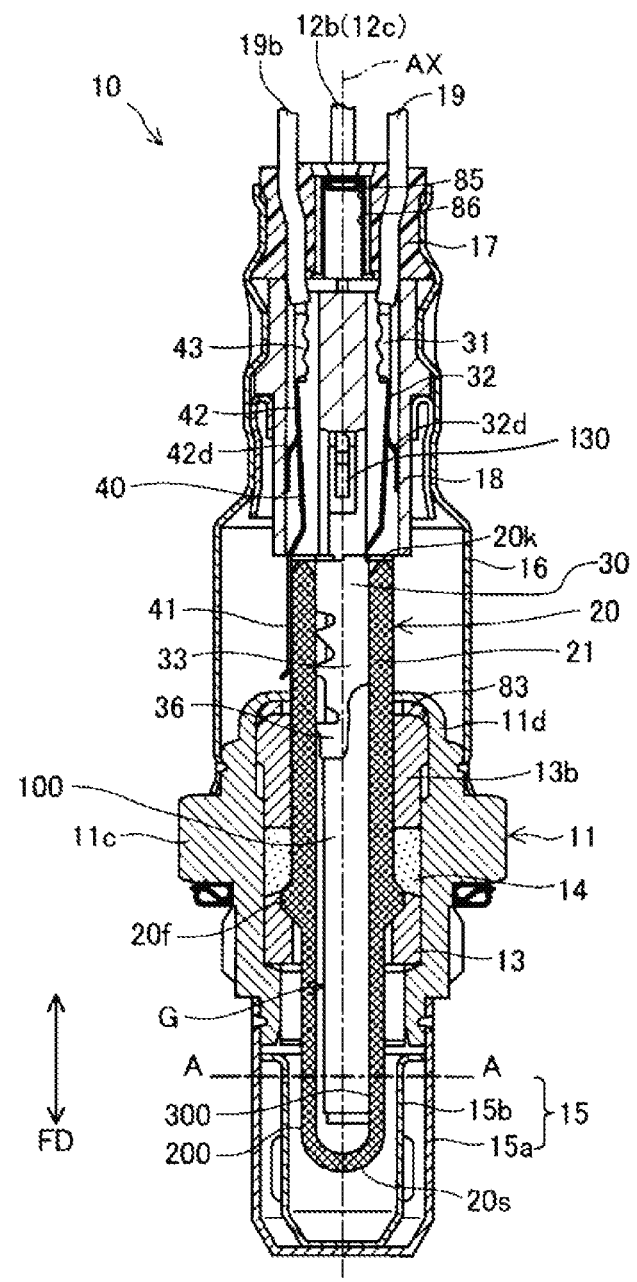
FIG. 1 is a sectional view showing the structure of a gas sensor.

Reference numerals used to identify various features in the drawings include the following.

10: gas sensor
11: metallic shell
11c: hexagonal portion
11d: connection portion
12b, 12c: heater lead wire
13, 13b: insulator
14: talc
15: protector
15a: outer protector
15b: inner protector
16: metal sleeve
17: grommet
18: separator
19, 19b: sensor output lead wire
20: gas sensor element
20f: flange portion
20s: bottomed portion
20t: base portion
21: solid electrolyte member
30: inside terminal member
31: connector portion
32: separator insertion portion
33: insertion portion
36: heater pressing portion
40: outside terminal member
41: outer fitting portion
42: separator insertion portion
42d: separator engagement portion
43: connector portion
83: metal packing
85: filter
86: metal pipe
100: ceramic heater
130: connection terminal
200: outside electrode
210: outside lead portion
214: longitudinal lead portion
217: ring lead portion
220: outside detection electrode portion
300: inside electrode
310: inside lead portion
320: inside detection electrode portion
400: heater energization control section
401: external connection bus
410: microprocessor
411: pulse signal output circuit
412: voltage shift circuit
413: output detection circuit
414: heater control circuit
415: I/O port
416: A/D input port
417: PWM output port
420: microprocessor

DETAILED DESCRIPTION OF THE PREFERRED EMBODIMENTS

The invention will next be described in greater detail with reference to the drawings. However, the present invention should not be construed as being limited thereto.

A. Structure of Gas Sensor

FIG. 1 is a sectional view showing the structure of a gas sensor 10 according to one embodiment of the present invention. The gas sensor 10 is an oxygen sensor for detecting oxygen contained in exhaust gas discharged from an internal combustion engine. The gas sensor 10 includes a gas sensor element 20, a metallic shell 11, an inside terminal member 30, an outside terminal member 40, and a ceramic heater 100 as main components.

FIG. 1 shows an axial line AX of the gas sensor 10. In the following description, of opposite ends of a member extending along the axial line AX, one end on the side where a solid electrolyte member 21 is disposed (the lower side of FIG. 1) will be referred to as the forward end, and the other end on the side where a grommet 17 is disposed (the upper side of FIG. 1) will be referred to as the rear end. Also, a longitudinal direction FD in FIG. 1 shows a direction parallel to the axial line AX (the vertical direction in FIG. 1).

The gas sensor element 20 has the shape of a bottomed tube extending in the direction of the axial line AX (the vertical direction in FIG. 1). The gas sensor element 20 has an approximately U-shaped cross section. The gas sensor element 20 has a bottomed portion 20s closed at its forward end (on the lower side of FIG. 1) and has a rear end 20k (on the upper side of FIG. 1) which forms an opening. The gas sensor element 20 includes the above-mentioned solid electrolyte member 21 having oxygen ion conductivity, an outside electrode 200 formed on a portion of the outer circumferential surface of the solid electrolyte member 21, and an inside electrode 300 formed on a portion of the inner circumferential surface of the solid electrolyte member 21. Also, a flange portion 20f projecting outward is provided on the outer circumferential surface of the gas sensor element 20 at an intermediate position in the direction of the axial line AX. The flange portion 20f engages the metallic shell 11 as described below.

The metallic shell 11 is formed to have a tubular shape and surrounds a portion of the outer circumference of the gas sensor element 20. An insulator 13 is disposed inside the metallic shell 11 with a metal packing (not shown) disposed therebetween. The flange portion 20f engages the insulator 13 with another metal packing (not shown) disposed therebetween. Further, talc 14, an insulator 13b, and a metal packing 83 are disposed on the rear end side of the insulator 13, and airtightly hold the gas sensor element 20 inside the metallic shell 11 as a result of crimping of a rear end portion of the metallic shell 11.

A protector 15 is attached to the forward end (on the lower side of FIG. 1) of the metallic shell 11. The protector 15 covers a forward end portion of the gas sensor element 20 projecting from an opening of the metallic shell 11 on the forward end side. The protector 15 has a double wall structure; i.e., includes an outer protector 15a and an inner protector 15b. Each of the outer protector 15a and the inner protector 15b has a plurality of gas passage holes through which the exhaust gas flows (not shown). The exhaust gas is supplied to the outside electrode of the gas sensor element 20 through the gas passage holes of the protector 15.

The metallic shell 11 has a connection portion 11d on the rear end side (the upper side of FIG. 1) of a hexagonal portion 11c formed on the outer circumferential surface of the metallic shell 11. The forward end of a tubular metal sleeve 16 is fixed to the connection portion 11d by means of laser welding; i.e., by applying a laser beam to the forward end of the metal sleeve 16 from the outer side over the entire circumference thereof. The above-mentioned grommet 17 formed of a fluororubber is inserted into an opening of the metal sleeve 16 on the rear end side. The grommet 17 is fixed by crimping a rear end portion of the metal sleeve 16. The grommet 17 seals the opening of the metal sleeve 16. A separator 18 formed of an insulating alumina ceramic is disposed on the forward end side of the grommet 17. Sensor output lead wires 19 and 19b and heater lead wires 12b and 12c extend through the grommet 17 and the separator 18. A through opening is formed at the center of the grommet 17 such that the through opening extends along the axial line AX, and a metal pipe 86 is fitted into the through opening. A sheet-shaped filter 85 having water repellency and gas permeability covers the metal pipe 86. As a result, the atmosphere outside the gas sensor 10 is introduced into the interior of the metal sleeve 16 through the filter 85, and then into an internal space G of the gas sensor element 20.

The outside terminal member 40 includes an outer fitting portion 41 formed of a stainless steel plate, a separator insertion portion 42, and a connector portion 43. The separator insertion portion 42 is inserted into the separator 18. A separator engagement portion 42d branches off and projects from the separator insertion portion 42. The separator engagement portion 42d elastically contacts the inner wall of the separator 18, whereby the outside terminal member 40 is held within the separator 18.

The connector portion 43 is provided at the rear end of the separator insertion portion 42. The connector portion 43 holds the conductor of the sensor output lead wire 19b fixed thereto by means of crimping and establishes electrical connection between the outside terminal member 40 and the sensor output lead wire 19b.

The outer fitting portion 41 is provided at the forward end of the separator insertion portion 42. The outer fitting portion 41 grasps the outer circumference of a portion of the gas sensor element 20 near the rear end thereof, and establishes electrical connection between the outside terminal member 40 and the outside electrode 200 of the gas sensor element 20. The electromotive force generated at the outside electrode 200 is output to the outside of the gas sensor 10 through the outside terminal member 40 and the sensor output lead wire 19b.

The inside terminal member 30 includes an insertion portion 33 formed of a stainless steel plate, a separator insertion portion 32, and a connector portion 31. The separator insertion portion 32 is inserted into the separator 18. A separator engagement portion 32d branches off and projects from the separator insertion portion 32. The separator engagement portion 32d elastically contacts the inner wall of the separator 18, whereby the inside terminal member 30 is held within the separator 18.

The connector portion 31 is provided at the rear end of the separator insertion portion 32. The connector portion 31 holds the conductor of the sensor output lead wire 19 fixed thereto by means of crimping, and establishes electrical connection between the inside terminal member 30 and the sensor output lead wire 19.

The insertion portion 33 is provided at the forward end of the separator insertion portion 32. The insertion portion 33 is inserted into the interior of the gas sensor element 20. By means of its elasticity, the insertion portion 33 comes into contact with the inside electrode 300 formed on the inner circumferential surface of the gas sensor element 20 while applying a pressing force thereto. As a result, the insertion portion 33 maintains electrical continuity to the inside electrode 300 of the gas sensor element 20. The electromotive force generated at the inside electrode 300 is output to the outside of the gas sensor 10 through the inside terminal member 30 and the sensor output lead wire 19.

A heater pressing portion 36 is provided at the forward end of the insertion portion 33. The heater pressing portion 36 presses the side surface of the ceramic heater 100 against the inner circumferential surface of the gas sensor element 20.

The ceramic heater 100 is disposed in the internal space G and is held by the inside terminal member 30, whereby the ceramic heater 100 maintains its attitude. Connection terminals 130 for the ceramic heater 100 are connected to the heater lead wires 12b and 12c. When electric power is supplied to the ceramic heater 100 from the heater lead wires 12b and 12c, the ceramic heater 100 heats the inner circumferential surface of the solid electrolyte member 21.

Figure 2A:
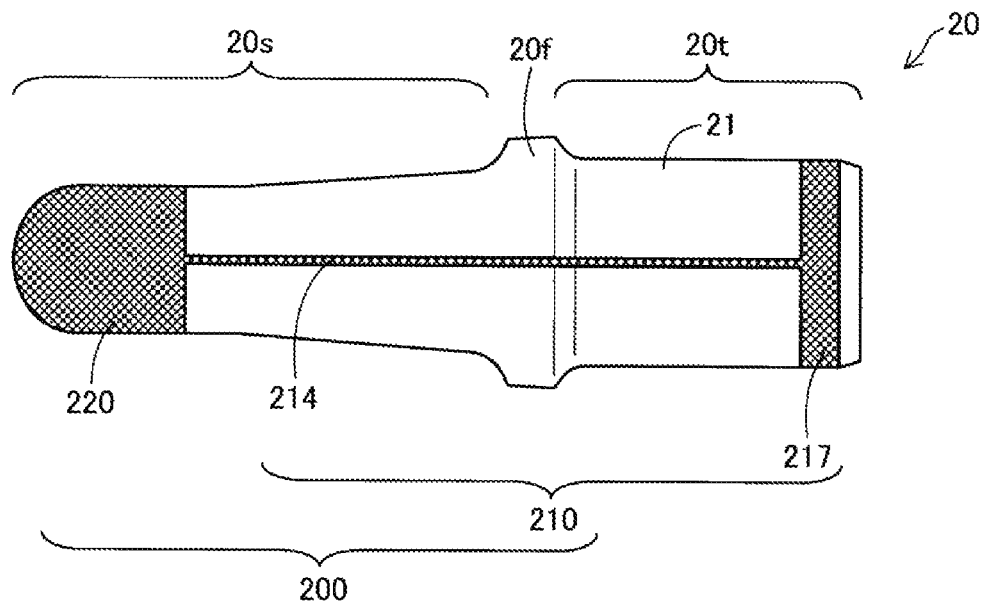
FIGS. 2A and 2B are explanatory views showing the structure of a gas sensor element according to one embodiment.

FIG. 2A shows the external appearance of a gas sensor element 20 according to one embodiment. The solid electrolyte member 21 of the gas sensor element 20 has the above-mentioned flange portion 20f, the bottomed portion 20s provided on the forward end side (on the left side of FIGS. 2A and 2B) of the flange portion 20f, and a base portion 20t provided on the rear end side of the flange portion 20f. The bottomed portion 20s is tapered such that its diameter gradually decreases toward the forward end side, and has a closed forward end. The base portion 20t generally has a hollow cylindrical shape and an opening at its rear end. The outside electrode 200 is formed on the outer surface of the solid electrolyte member 21.

The outside electrode 200 has an outside lead portion 210 and an outside detection electrode portion 220. The outside detection electrode portion 220 covers the outer surface of a forward-end-side portion of the bottomed portion 20s of the solid electrolyte member 21. The outside detection electrode portion 220 is provided at a position where it comes into contact with a gas under measurement. The outside detection electrode portion 220 constitutes an oxygen concentration cell in cooperation with an inside electrode detection portion (described below) of the inside electrode 300 and the solid electrolyte member 21, and generates a voltage corresponding to the gas concentration of the gas under measurement.

The outside lead portion 210 is connected to the rear end of the outside detection electrode portion 220. The outside lead portion 210 has a longitudinal lead portion 214 and a ring lead portion 217. The ring lead portion 217 is formed on the base portion 20t at a position near the rear end thereof such that the ring lead portion 217 extends over the entire circumference of the gas sensor element 20 and forms an annular shape. The longitudinal lead portion 214 is formed to linearly extend along the direction of the axial line O and establish connection between the rear end of the outside detection electrode portion 220 and the ring lead portion 217. Notably, an electrode protection layer (not shown) for protecting the outside detection electrode portion 220 may be formed on the surface of the outside detection electrode portion 220. Also, the outside detection electrode portion 220 and the outside lead portion 210 may be formed of the same electrically conductive material (for example, electrically conductive oxide described below). Notably, the shape and layout of the outside electrode 200 are only examples, and various other shapes and layouts can be employed.

The solid electrolyte member 21 is formed of a solid electrolyte including $ZrO_2$ which has oxygen-ion conductivity. Generally, a stabilized zirconia including a stabilizer added thereto is used as the solid electrolyte. An oxide selected from yttrium oxide ($Y_2O_3$), calcium oxide (CaO), magnesium oxide (MgO), cerium oxide ($CeO_2$), ytterbium oxide ($Yb_2O_3$), scandium oxide ($Sc_2O_3$), etc., can be used as a stabilizer.

Figure 2B:
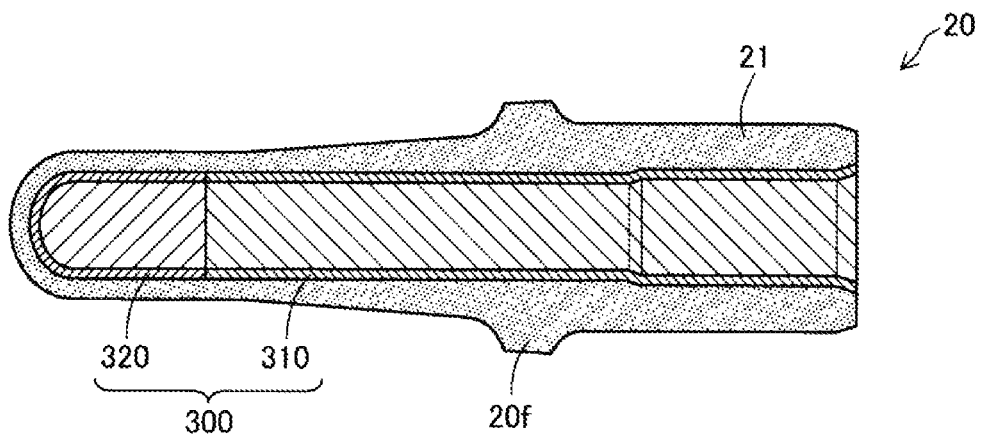

FIG. 2B is a longitudinal sectional view of the gas sensor element 20. As described above, the inside electrode 300 (air reference electrode) is provided on the inner surface of the solid electrolyte member 21. The inside electrode 300 has an inside lead portion 310 and an inside detection electrode portion 320.

The inside detection electrode portion 320 is formed to cover the inner surface of a forward-end-side portion of the solid electrolyte member 21. The inside lead portion 310 is connected to the rear end of the inside detection electrode portion 320 and is in contact with the inside terminal member 30 (FIG. 1) for electrical connection therewith. The inside detection electrode portion 320 and the inside lead portion 310 as a whole covers substantially the entire inner surface of the solid electrolyte member 21. In the example of FIG. 2B, the boundary between the inside detection electrode portion 320 and the inside lead portion 310 is located on the forward end side of the flange portion 20f of the solid electrolyte member 21. However, the boundary between the inside detection electrode portion 320 and the inside lead portion 310 may be located at a different position. Also, the inside detection electrode portion 320 and the inside lead portion 310 may be formed of the same electrically conductive material (for example, an electrically conductive oxide described below). In this case, no boundary is present between the inside detection electrode portion 320 and the inside lead portion 310.

The outside electrode 200 and the inside electrode 300 constitute an electrode portion of the gas sensor element 20. The outside electrode 200 and the inside electrode 300 can be formed of an electrically conductive oxide or a noble metal such as platinum (Pt) or gold (Au). The entire outside electrode 200 and the entire inside electrode 300 may be formed of an electrically conductive oxide. Alternatively, a portion of the outside electrode 200 and a portion of the inside electrode 300 may be formed of an electrically conductive oxide, and the remaining portion of the outside electrode 200 and the remaining portion of the inside electrode 300 may be formed of a noble metal. However, in order to accurately perform internal resistance control, a portion of the electrode portion including the outside electrode 200 and the inside electrode 300 is preferably formed of an electrically conductive oxide. Also, in consideration of detection performance, the outside detection electrode portion 220 of the outside electrode 200 is preferably formed of a noble metal. Particularly, at least one of the outside lead portion 210 and the inside lead portion 310 is preferably formed of an electrically conductive oxide. The reason for this will be described in detail below.

The electrically conductive oxide used to form the electrode portion of the gas sensor element 20 preferably contains one of the following perovskite phases as a main component.

(i) Perovskite phase which is represented by a composition formula of $LaCo_{1-x}Ni_xO_{3\pm d}$ ($0.300 \le x \le 0.600$, $0 \le d \le 0.4$) and has a perovskite-type crystal structure.

(ii) Perovskite phase which is represented by a composition formula of $LaFe_{1-y}Ni_yO_{3\pm d}$ ($0.450 \le y \le 0.700$, $0 \le d \le 0.4$) and has a perovskite-type crystal structure.

These perovskite phases; i.e., LCN and LFN, have good characteristics; i.e., their electrical conductivities at room temperature (25° C.) are equal to or greater than 200 S/cm, and the absolute values of their B constants (25° C. to 570° C.) are smaller than the absolute value of the B constant (25° C. to 570° C.) of platinum. When the electrical conductivity at room temperature (25° C.) is equal to or greater than 200 S/cm, the electrically conductive oxide used as an electrode material can have a sufficiently high electrical conductivity. Also, when the absolute value of the B constant (25° C. to 570° C.) is smaller than that of platinum, the internal resistance control can be performed accurately as compared to the case where platinum is used as the material for the electrode portion.

Notably, from the viewpoint of more accurately performing the internal resistance control, the coefficient x of LCN preferably satisfies a relation of $0.550 \le x \le 0.600$ or the coefficient y of LFN satisfies a relation of $0.500 \le y \le 0.550$ or a relation of $0.650 \le y \le 0.700$.

The coefficient d of O (oxygen) in the above-described formulas is theoretically 0 in the case where all the electrically conductive oxide having the above-described composition is formed of the perovskite phase. However, since the proportion of oxygen may deviate from the stoichiometric composition, as a typical example, the range of d is defined to be $0 \le d \le 0.4$.

Notably, the electrically conductive oxide which forms the electrode portion may contain other oxides so long as the electrically conductive oxide contains the above-described LCN or LFN as a main component. For example, the electrically conductive oxide may contain LCN or LFN as a main component and may also contain, as a secondary component, ceria to which a rare earth element oxide other than ceria is added (hereinafter referred to as "rare earth element-added ceria"). Notably, the rare earth element-added ceria will be also referred to as a "co-material." For example, $La_2O_3$, $Gd_2O_3$, $Sm_2O_3$, and/or $Y_2O_3$ may be used as a rare earth element oxide other than ceria. The proportion of the rare earth element RE in the rare earth element-added ceria may be determined such that the molar fraction of the rare earth element RE represented by an expression of $\{RE/(Ce+RE)\}$ falls within the range of, for example, 10 mol % to 50 mol %. Also, the volume ratio of the rare earth element-added ceria in the electrically conductive oxide may be set to fall within the range of, for example, 10 vol % to 40 vol %. Although such a rare earth element-added ceria is an insulator at low temperature (room temperature), it functions as a solid electrolyte having oxygen-ion conductivity at high temperature (temperatures at which the gas sensor 10 is used). Accordingly, when the electrically conductive oxide contains the rare earth element-added ceria, it is possible to lower the resistance of the electrically conductive oxide during use of the gas sensor 10. However, in order to lower the electrical resistance at room temperature, the electrically conductive oxide desirably contains no rare earth element-added ceria.

The electrically conductive oxide may contain an alkaline earth metal element in a very small amount so long as the alkaline earth metal element does not affect the electrical conductivity of the electrically conductive oxide. However, preferably, the electrically conductive oxide is substantially free of alkaline earth metal element. In such a case, even when the electrode portion containing the electrically conductive oxide is exposed to a wide range of temperature ranging from room temperature to a temperature near 900° C. during use of the gas sensor 10, a change in the weight of the electrically conductive oxide; i.e., absorption or release of oxygen, becomes less likely to occur. As a result, an electrode structure suitable for use in a high temperature environment is obtained. Notably, in the present specification, "substantially free of alkaline earth metal element" means that no alkaline earth metal element can be detected or identified by x-ray fluorescence analysis (XRF).

B. Circuit Configuration of Gas Sensor Control Apparatus

Figure 3:
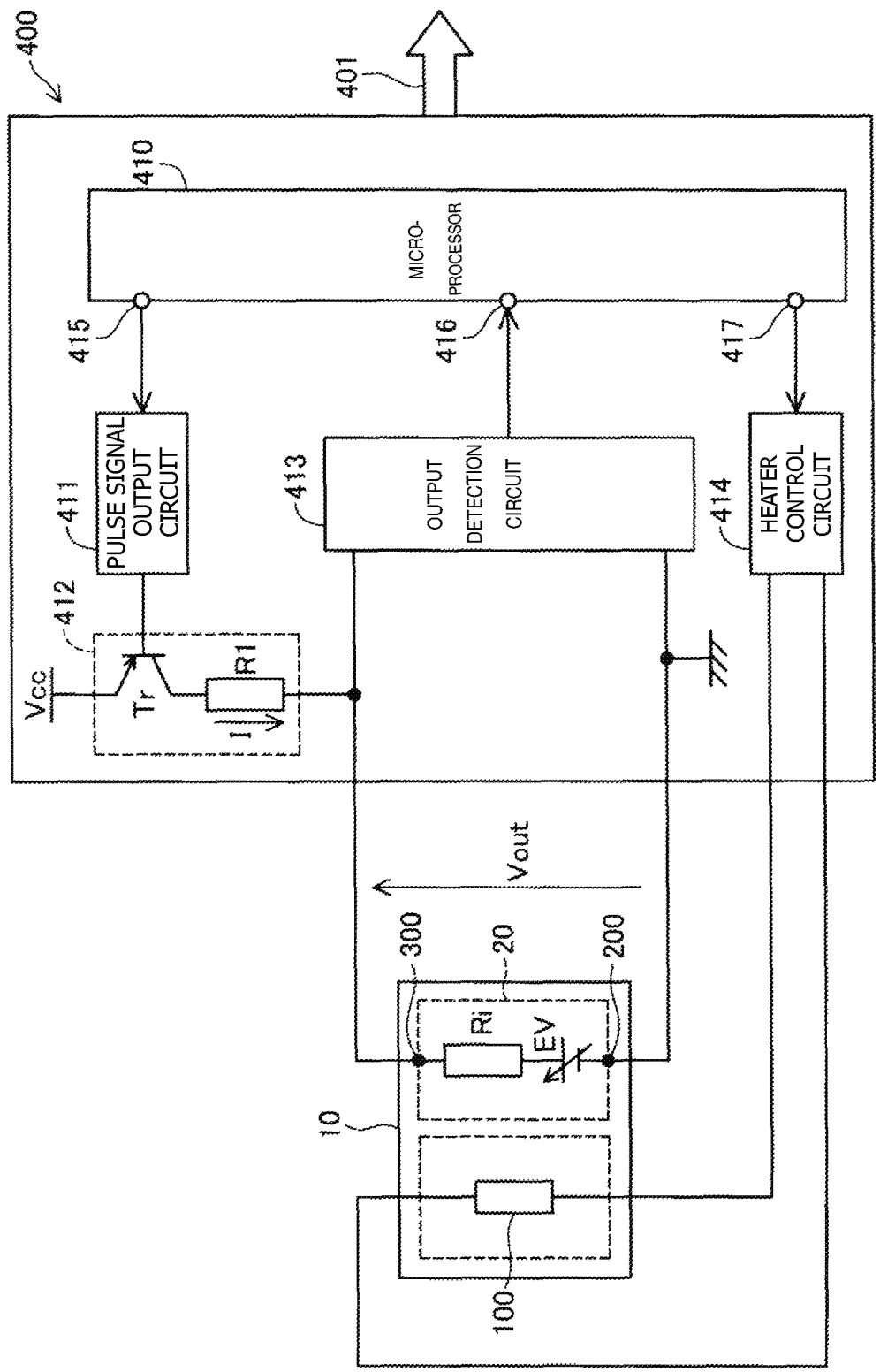
FIG. 3 is a diagram schematically showing the configuration of a gas sensor control apparatus.

FIG. 3 is a diagram schematically showing the configuration of a gas sensor control apparatus which includes the gas sensor 10 and a heater energization control section 400 which is connected to the gas sensor 10 and serves as a sensor output processing apparatus. This gas sensor control apparatus is mounted on, for example, a vehicle (not shown) including an internal combustion engine. The heater energization control section 400 controls the gas sensor 10 and processes the output of the gas sensor 10 which changes with the concentration of oxygen contained in exhaust gas discharged from the internal combustion engine, to thereby determine whether or not combustion in the internal combustion engine is on the rich side or lean side with respect to the stoichiometric air-fuel ratio. The heater energization control section 400 sends the detected output of the gas sensor 10 to an external apparatus (for example, an ECU) through an external connection bus 401.

As described above, the gas sensor 10 includes the gas sensor element 20 having the outside electrode 200 and the inside electrode 300, and the ceramic heater 100. In a state in which the gas sensor element 20 is maintained at a proper activation temperature (about 500° C. to 600° C.), the gas sensor element 20 exhibits good oxygen ion conductivity, generates an electromotive force EV between the electrodes 200 and 300 in proportion to the oxygen concentration, and outputs a sensor output Vout. In addition, in this gas sensor 10, the supply of electric current to the ceramic heater 100 is controlled by the heater energization control section 400 such that the temperature of the gas sensor element 20 is maintained within a predetermined range within which the gas sensor element 20 is active. The ceramic heater 100 is connected to a heater control circuit 414 of the heater energization control section 400.

The gas sensor element 20 has an internal resistor Ri whose resistance decreases when the temperature of the gas sensor element 20 rises. Namely, a negative correlation exists between the internal resistance Ri and the element temperature of the gas sensor element 20. Therefore, the element temperature can be maintained within the predetermined range by performing the internal resistance control such that the internal resistance Ri falls within a range of a target resistance±an allowable error.

The heater energization control section 400 includes a microprocessor 410, a pulse signal output circuit 411, a voltage shift circuit 412, an output detection circuit 413, and the heater control circuit 414. The heater control circuit 414 is connected to a PWM (pulse-width-modulated) output port 417 of the microprocessor 410. Electric current is supplied to the ceramic heater 100 of the gas sensor 10 as a result of PWM control performed by the heater control circuit 414, whereby the gas sensor element 20 is heated. For example, in order to maintain the temperature of the gas sensor element 20 within the predetermined range, the duty ratio of pulses used for the PWM control is determined by PID (proportional-integral-derivative) control or PI (proportional-integral) control performed by the microprocessor 420.

The outside electrode 200 and the inside electrode 300 of the gas sensor element 20 are connected to the output detection circuit 413. The output detection circuit 413 inputs the electromotive force EV of the gas sensor element 20 to an A/D input port 416 of the microprocessor 410 as a sensor output Vout. Notably, since the outside electrode 200 of the gas sensor element 20 is maintained at the reference potential (GND) of the output detection circuit 413, the inside electrode 300 assumes a positive high potential relative to the potential of the outside electrode 200.

In addition to the output detection circuit 413, the voltage shift circuit 412 is connected to the inside electrode 300 of the gas sensor element 20. The voltage shift circuit 412 connects the inside electrode 300 to a line of a power supply voltage Vcc through a reference resistor R1 and a switching device Tr. The pulse signal output circuit 411 is connected to the switching device Tr of the voltage shift circuit 412. This pulse signal output circuit 411 is connected to an I/O port 415 of the microprocessor 410. In response to an instruction from the microprocessor 410, the pulse signal output circuit 411 drives the voltage shift circuit 412 so as to produce a temporary change in the current flowing between the electrodes of the gas sensor element 20. Specifically, the pulse signal output circuit 411 turns on the switching device Tr of the voltage shift circuit 412 so that a current flows from the line of the power supply voltage Vcc to the reference resistance R1 and the gas sensor element 20. As a result, the sensor output Vout between the electrodes of the gas sensor element 20 changes in accordance with a voltage drop produced by the internal resistor Ri of the gas sensor element 20. Therefore, it is possible to calculate the voltage drop produced by the internal resistor Ri from the difference between the sensor output Vout before the switching device Tr of the voltage shift circuit 412 is turned on and the sensor output Vout after the switching device Tr of the voltage shift circuit 412 is turned on; i.e., from the amount of a response change in the voltage, to thereby detect the internal resistance Ri of the gas sensor element 20. Thus, the element temperature can be maintained within the active temperature range by controlling the ceramic heater 100 such that the internal resistance Ri coincides with a target resistance. Notably, the configuration of the heater energization control section 400 shown in FIG. 3 is an example, and various other configurations can be employed.

Within the active temperature range, the gas sensor element 20 exhibits oxygen ion conductivity, functions as an oxygen concentration cell, and generates an electromotive force EV in proportion to the difference in oxygen concentration between the outside electrode 200 and the inside electrode 300. Therefore, in an equivalent circuit of the gas sensor element 20, the cell (oxygen concentration cell) generating the electromotive force EV and the internal resistor Ri are connected in series between the electrodes 200 and 300.

Figure 4:
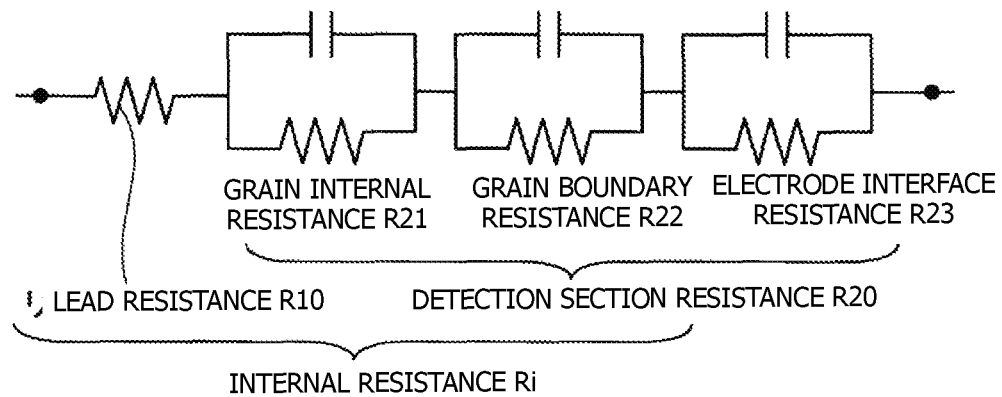
FIG. 4 is an equivalent circuit showing the details of the internal resistance of the gas sensor element.

FIG. 4 is an equivalent circuit which shows the detail of the internal resistor Ri of the gas sensor element 20. The internal resistance Ri is composed of a lead resistance R10 and a detection portion resistance R20. The lead resistance R10 is the sum of the electrical resistance of the outside electrode 200 (FIG. 2) and the electrical resistance of the inside electrode 300. The detection portion resistance R20 is the electrical resistance of the detection portion constituted by the outside detection electrode portion 220, the inside detection electrode portion 320, and the solid electrolyte member 21 sandwiched between the two electrode portions. The detection portion resistance R20 can be divided into a grain internal resistance R21, a grain boundary resistance R22, and an electrode interface resistance R23. The grain internal resistance R21 and the grain boundary resistance R22 are resistances within the solid electrolyte member 21. More accurately, as shown in FIG. 4, the equivalent circuit includes three capacitors connected in parallel to the three resistors having the resistances R21, R22, and R23.

In this equivalent circuit, the detection portion resistance R20 has a negative correlation with temperature. Meanwhile, in the case where all the outside electrode 200 and the inside electrode 300 are formed of platinum, the lead resistance R10 has a positive correlation with temperature. In the case where the entire internal resistance Ri has a negative correlation with temperature, the element temperature can be maintained within a predetermined range by controlling the internal resistance Ri to a fixed value. However, since the resistance of platinum has a positive correlation with temperature, when the amount of change in the lead resistance R10 with temperature is large, a problem arises in that even when internal resistance control is performed, the accuracy of control of the element temperature is not sufficient, and the element temperature cannot be controlled to fall within a predetermined range. Particularly, the above-mentioned problem becomes remarkable in the case where the lead resistance is increased by reducing the amount of platinum for cost reduction.

In view of the above, in the present embodiment, at least a portion of the electrode portion (the outside electrode 200 and the inside electrode 300) of the gas sensor element 20 is formed of an electrically conductive oxide including the above-described LCN or LFN as a main component. Since the absolute values of the B constants (25° C. to 570° C.) of LCN and LFN are smaller than the absolute value of the B constant (25° C. to 570° C.) of platinum, as described below, the amount of change in the lead resistance R10 with temperature can be reduced as compared to the case where the electrode portion is formed of platinum only. Accordingly, when the internal resistance control is performed, the element temperature can be controlled with increased accuracy.

C. Method of Manufacturing Gas Sensor Element

Figure 5:
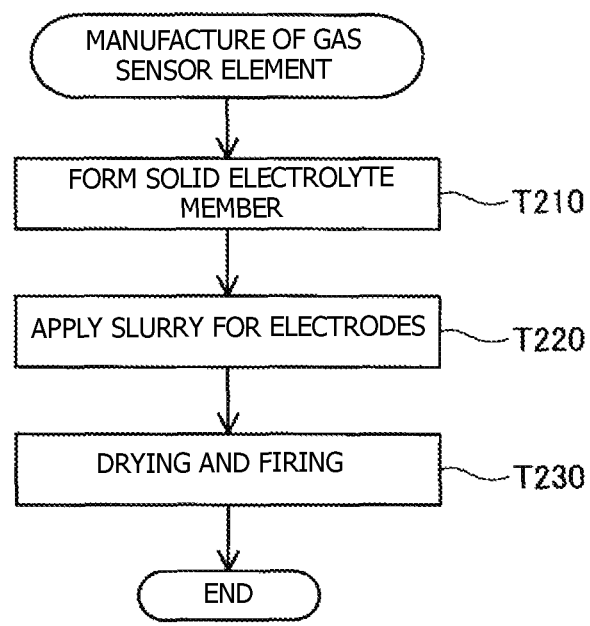
FIG. 5 is a flowchart showing a method of manufacturing the gas sensor element.

FIG. 5 is a flowchart showing a method of manufacturing the gas sensor element 20 shown in FIG. 2. In step T210, the material (e.g., powder of yttria-stabilized zirconia) of the solid electrolyte member 21 is pressed to obtain a compact, which is then machined into a shape (tubular shape) shown in FIG. 2, whereby a green body (green compact) is obtained.

In step T220, a paste (or slurry) of an electrode material for forming the electrodes is prepared and is applied to the solid electrolyte member 21. A paste (or slurry) of an electrically conductive oxide which contains the above-described LCN or LFN as a main component and a paste of platinum can be used as an electrode material. In the following, the case where the paste of an electrically conductive oxide is mainly used for the inside electrode 300 will be described. When the paste of the electrically conductive oxide is prepared, for example, source powders of the electrically conductive oxide are weighed and wet-mixed, and the resultant mixture is dried, whereby a source powder mixture is prepared. For example, $LaOH_3$ or $La_2O_3$, $Co_3O_4$, $Fe_2O_3$, and NiO may be used as the source powder of LCN or LFN. Also, $CeO_2$ and $La_2O_3$, $Gd_2O_3$, $Sm_2O_3$, $Y_2O_3$, etc., may be used as the source powder of the rare earth element-added ceria. The mixture of these source powders is calcined at 700 to 1,200° C. for 1 to 5 hours in the atmosphere, whereby a calcined powder is prepared. This calcined powder is dissolved, together with a binder such as ethyl cellulose, in a solvent such as terpineol or butyl carbitol, whereby a paste is prepared. In step T220, the paste of the electrically conductive oxide is applied to the entire region corresponding to the inside electrode 300 (FIG. 2). Notably, as to the outside electrode 200, a paste of a noble metal (for example, Pt or Au) is applied.

In step T230, after drying, the green compact is fired at a firing temperature of, for example, 1,250° C. to 1,450° C. (preferably, 1,350±50° C.). As a result, the structure shown in FIG. 2 is obtained. Notably, the above-described various manufacturing conditions are only examples, and can be freely changed in accordance with use of products or the like.

D. Characteristic of Electrically Conductive Oxide

Table 1 below shows the compositions of electrode materials and their electrical characteristics (electrical conductivity and B constant) determined by an experiment. LCN ($LaCo_{1-x}Ni_xO_{3\pm d}$) is used for samples S11 to S18. However, the value of the coefficient x differs among these samples in the range of 0.0 to 0.700. LFN ($LaFe_{1-y}Ni_yO_{3\pm d}$) is used for samples S21 to S28. However, the value of the coefficient y differs among these samples in the range of 0.0 to 0.800. Platinum (Pt) is used for sample S31. The room temperature electrical conductivity and the B constant $B_{25-570}$ of each sample are shown in columns on the right side of Table 1.

TABLE 1

| Sample | Composition formula | x or y | Conductivity (25° C.) S/cm | B constant $B_{25-570}$ $K^{-1}$ |
|---|---|---|---|---|
| S11 | $LaCo_{1-x}Ni_xO_{3\pm d}$ | 0.000 | 0.33 | 3680 |
| S12 | (LCN) | 0.100 | 45 | 1351 |
| S13 | | 0.200 | 148 | 916 |
| S14 | | 0.300 | 461 | 464 |
| S15 | | 0.400 | 1037 | 123 |
| S16 | | 0.500 | 1903 | −44 |
| S17 | | 0.600 | 275 | 331 |
| S18 | | 0.700 | 83 | 839 |
| S21 | $LaFe_{1-y}Ni_yO_{3\pm d}$ | 0.100 | 0.52 | 1529 |
| S22 | (LFN) | 0.300 | 8.4 | 1199 |
| S23 | | 0.450 | 201 | 138 |
| S24 | | 0.500 | 298 | 218 |
| S25 | | 0.550 | 581 | 19 |
| S26 | | 0.600 | 821 | −10 |
| S27 | | 0.700 | 363 | 36 |
| S28 | | 0.800 | 175 | 297 |
| S31 | Pt | — | — | −589 |

The B constant $B_{25-570}$ is calculated in accordance with the following equations from the electrical conductivity at 25° C. and the electrical conductivity at 570° C.

$B = \ln(\rho 1/\rho 2)/(1/T1 - 1/T2)$ $\rho 1 = 1/\sigma 1$ $\rho 2 = 1/\sigma 2$ ρ1: resistivity (Ωcm) at an absolute temperature T1((K)
ρ2: resistivity (Ωcm) at an absolute temperature T2((K)
σ1: electrical conductivity (S/cm) at the absolute temperature T1(K)
σ2: electrical conductivity (S/cm) at the absolute temperature T2(K)
T1=298.15(K)
T2=843.15(K)

Figure 6A:
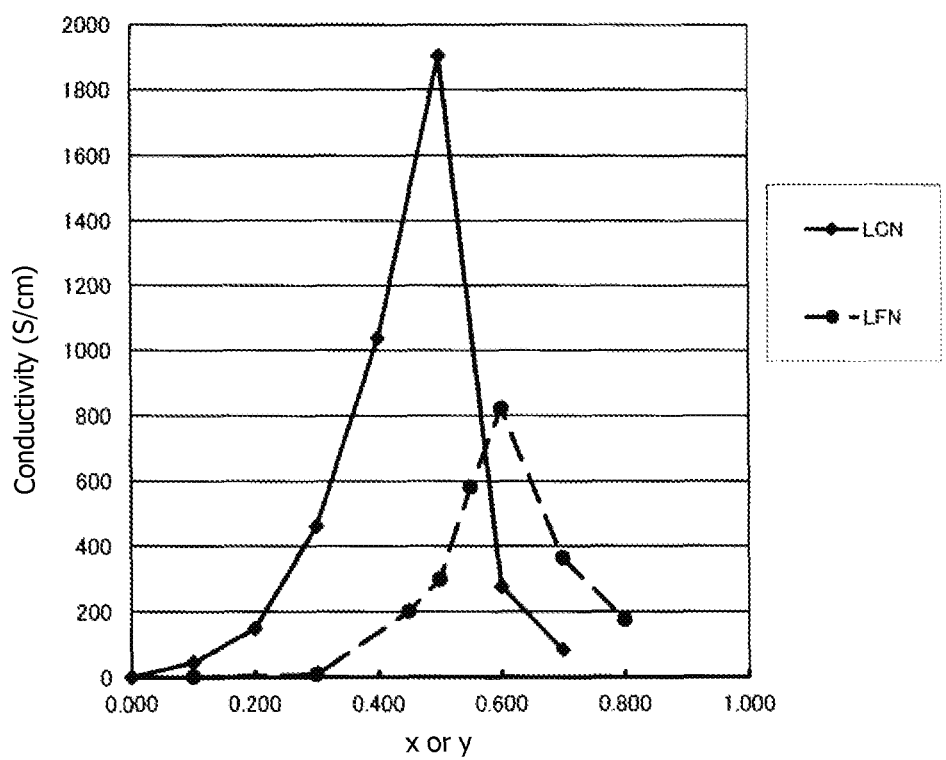
FIGS. 6A and 6B are graphs each showing the relation between the coefficient x or y of the perovskite phase and electrical characteristics.
Figure 6B:
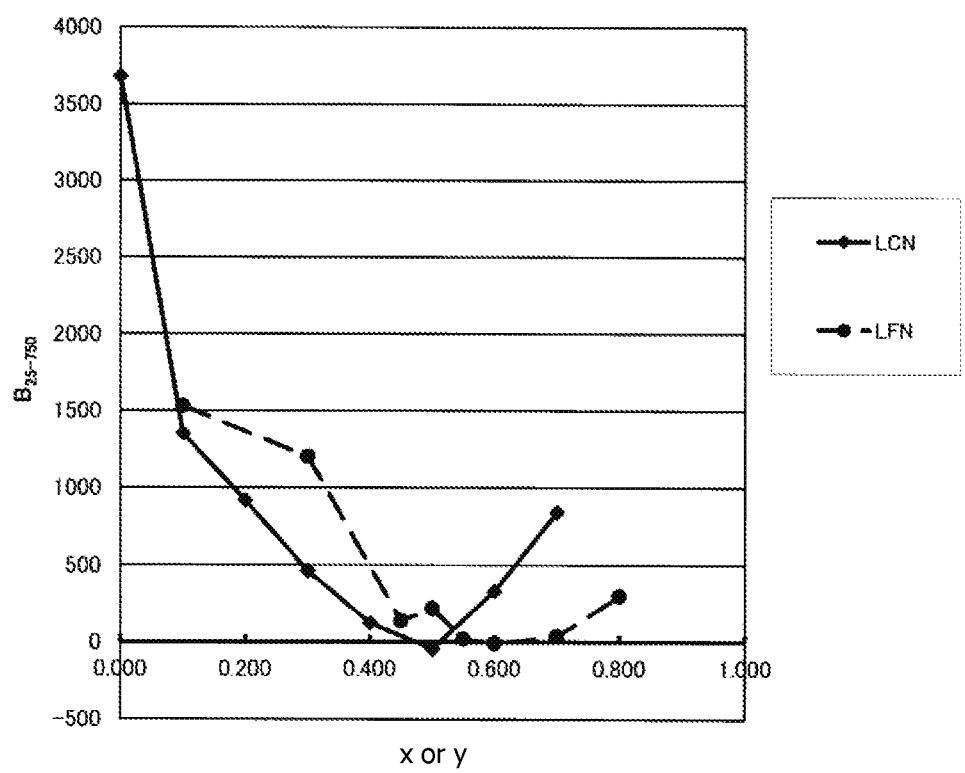

FIGS. 6A and 6B illustrate the relation between the coefficient x or y and electrical characteristics (electrical conductivity and B constant) for LCN and LFN shown in Table 1. The results shown in Table 1 and FIGS. 6A and 6B reveal the following points.

(1) In the case of LCN, when the value of the coefficient x falls within the range of 0.300 to 0.600, the room temperature electrical conductivity is 200 S/cm or greater, and the absolute value of the B constant $B_{25\text{-}570}$ is smaller than that of platinum. Therefore, the value of the coefficient x preferably falls within the range of 0.300 to 0.600.

(2) In the case of LFN, when the value of the coefficient y falls within the range of 0.450 to 0.700, the room temperature electrical conductivity is 200 S/cm or greater, and the absolute value of the B constant $B_{25\text{-}570}$ is smaller than that of platinum. Therefore, the value of the coefficient y preferably falls within the range of 0.450 to 0.700.

Notably, in general, when the B constant is positive, the resistance temperature coefficient is negative, and when the B constant is negative, the resistance temperature coefficient is positive. Accordingly, the use of LCN or LFN whose B constant is positive is particularly preferred so as to make the resistance temperature coefficient of the lead resistance R10 (FIG. 4) negative. Specifically, the preferred ranges for the coefficients x and y are as follows.

(3) In the case of LCN, the value of the coefficient x which satisfies the relation of 0.550≤x≤0.600 is particularly preferred.

(4) In the case of LFN, the value of the coefficient y which satisfies the relation of 0.500≤y≤0.550 or the relation of 0.650≤y≤0.700 is particularly preferred.

When the values of the coefficients x and y fall within their ranges, the room temperature electrical conductivity becomes sufficiently high, and the B constant $B_{25\text{-}570}$ becomes a positive value, so that the resistance temperature coefficient becomes negative. Therefore, the accuracy of the element temperature control by the internal resistance control can be further improved.

Figure 7:
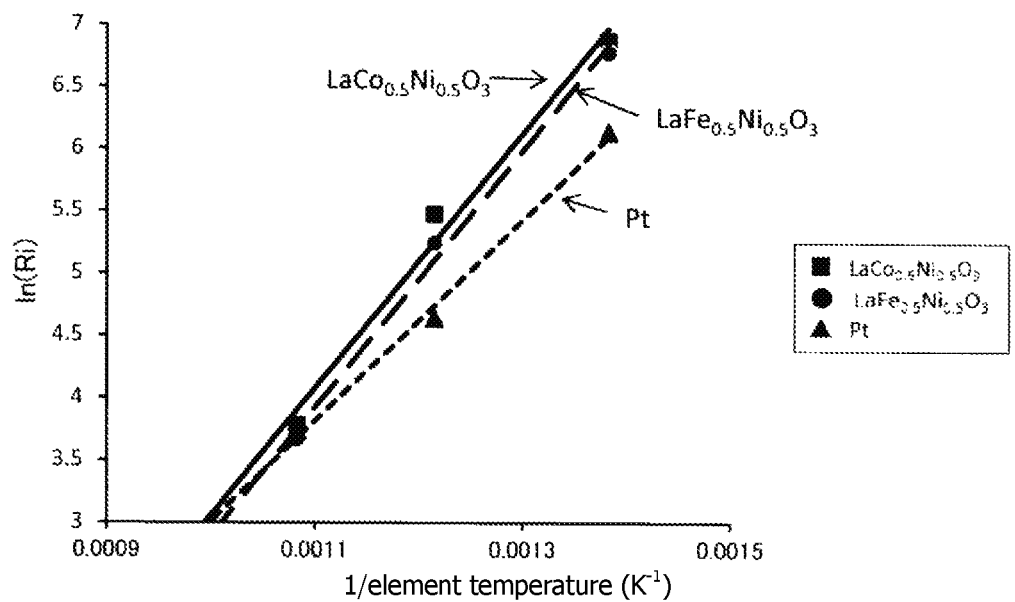
FIG. 7 is a graph showing the relation between element temperature and internal resistance for three types of electrode materials.

FIG. 7 is a graph showing the relation between the element temperature and the internal resistor Ri for sample S16 ($LaCo_{0.5}Ni_{0.5}O_3$), sample S25 ($LaFe_{0.5}Ni_{0.5}O_3$), and sample S31 (Pt) shown in Table 1. The horizontal axis shows the reciprocal of the element temperature and the vertical axis shows the natural logarithm of the internal resistance Ri. In the graph of FIG. 7, the greater the inclination, the narrower the temperature range corresponding to a variation in the internal resistance Ri. Accordingly, under the assumption that the controllable range of the internal resistance Ri (=the target value of Ri±an allowable error) is constant, the greater the inclination of each line in the graph of FIG. 7, the higher the accuracy with which the element temperature can be controlled to a predetermined temperature. In other words, the greater the inclination of each line in the graph of FIG. 7, the higher the accuracy with which the element temperature can be controlled to the predetermined temperature by means of the internal resistance control. In the example shown in FIG. 7, since the inclinations of the lines for LCN and LFN are greater than that of the line for platinum, the element temperature can be controlled to the predetermined temperature more accurately by means of the internal resistance control.

Modifications:

Notably, the present invention is not limited to the above-described examples and embodiments and can be implemented in various forms without departing from the scope of the invention.

Modification 1:

In the above-described embodiments, an oxygen concentration sensor has been described as an example of a gas sensor. However, the present invention can be applied to an oxygen sensor having a different structure and a gas sensor for a gas other than oxygen.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2015-170215 filed Aug. 31, 2015, the above-noted application incorporated herein by reference in its entirety.

What is claimed is:

1. A gas sensor control apparatus comprising:
   a gas sensor element which includes a solid electrolyte member and an electrode portion, the electrode portion including an outside electrode which is provided on an outer surface of the solid electrolyte member and which comes into contact with a gas under measurement, and an inside electrode which is provided on an inner surface of the solid electrolyte member and which comes into contact with a reference gas;
   a heater for heating the gas sensor element; and
   heater energization control means for feedback controlling energization of the heater such that an internal resistance of the gas sensor element coincides with a target resistance,
   wherein at least a portion of the electrode portion is formed of an electrically conductive oxide whose main component is
   (i) a perovskite phase which is represented by a composition formula of $LaCo_{1-x}Ni_xO_{3\pm d}$ (0.55≤x≤0.600, 0≤d≤0.4) and has a perovskite-type crystal structure, or
   (ii) a perovskite phase which is represented by a composition formula of $LaFe_{1-y}Ni_yO_{3\pm d}$ (0.55≤y≤0.700, 0≤d≤0.4) and has a perovskite-type crystal structure, and
   wherein
   the outside electrode includes an outside lead portion and an outside detection electrode portion which comes into contact with the gas under measurement;
   the outside detection electrode portion is formed of a noble metal; and
   the outside lead portion is formed of the electrically conductive oxide.

2. The gas sensor control apparatus as claimed in claim 1, wherein
   in the composition formula of $LaFe_{1-y}Ni_yO_{3\pm d}$ (0.650≤y≤0.700).

* * * * *